Figure 1:
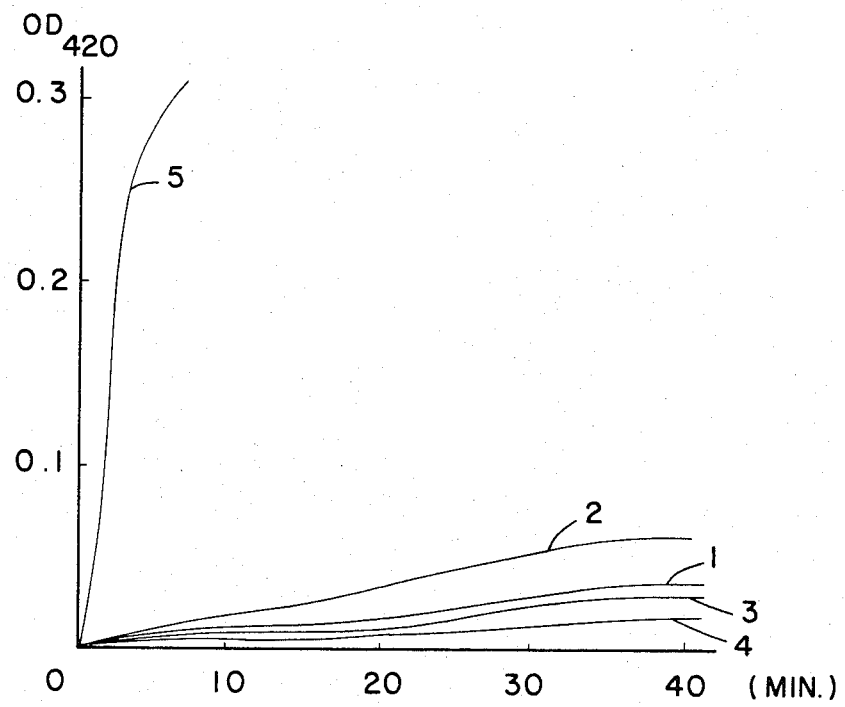

United States Patent [19]

Hashimoto

[11] Patent Number: 4,526,779
[45] Date of Patent: Jul. 2, 1985

[54] TOPICAL SKIN DEPIGMENTING COMPOSITION

[75] Inventor: Akira Hashimoto, Takatsuki, Japan

[73] Assignee: Sunstar Kabushi Kaisha, Takatsuki, Japan

[21] Appl. No.: 351,670

[22] Filed: Feb. 26, 1982

[30] Foreign Application Priority Data

Mar. 5, 1981 [JP] Japan .................................. 56-32260

[51] Int. Cl.$^3$ ............................................ A61K 7/135
[52] U.S. Cl. ...................... 424/62; 560/144; 514/546; 514/548; 514/549
[58] Field of Search ............... 424/62, 331, 311, 312; 560/144

[56] References Cited

U.S. PATENT DOCUMENTS

| | | | |
|---|---|---|---|
| 2,799,698 | 7/1957 | Tanes | 560/144 |
| 2,880,140 | 3/1959 | de Navarre | 424/60 |
| 3,294,836 | 12/1966 | Peterson et al. | 560/144 |
| 3,856,934 | 12/1974 | Kligman | 424/62 |
| 4,136,166 | 1/1979 | Barnett et al. | 424/62 |
| 4,164,564 | 8/1979 | Chen | 424/62 |
| 4,234,733 | 11/1980 | Isshiki et al. | 560/144 |

FOREIGN PATENT DOCUMENTS

| | | | |
|---|---|---|---|
| 45-15391 | 5/1970 | Japan | 424/62 |
| 6910088 | 1/1971 | Netherlands | 560/144 |

*Primary Examiner*—Dale R. Ore
*Attorney, Agent, or Firm*—Wegner & Bretschneider

[57] ABSTRACT

A stable topical skin depigmenting composition having no irritant action to the skin which comprises an active ingredient a fatty acid ester of hydroquinone of the formula:

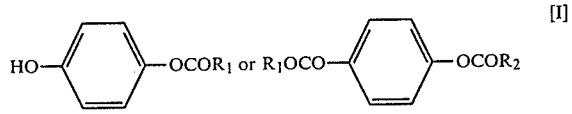

[I]

wherein $R_1$ and $R_2$ are the same or different, each being hydrogen or a straight or branched, saturated or unsaturated aliphatic hydrocarbon radical having 1 to 20 carbon atoms, provided that at least one of $R_1$ and $R_2$ is the hydrocarbon radical and one or more conventional ingredients suitable for a topical preparation. A method of depigmentation of the skin using the ester of the formula [I] is also disclosed.

1 Claim, 1 Drawing Figure

TOPICAL SKIN DEPIGMENTING COMPOSITION

The present invention relates to a skin depigmenting composition for topical use.

It has been known that hydroquinone and various derivatives thereof inhibit the formation of melanin and many of them have been expected to be useful for depigmentation of the skin. However, the only compound which can be practically used for depigmentation of the skin is hydroquinone.

Although a topical skin depigmenting composition containing hydroquinone, for example, an ointment containing hydroquinone has been used for a long time, it produces undesirable side effects such as irritation to the skin.

Recently, in order to eliminate irritant action of a hydroquinone-containing preparation to the skin, it has been proposed to incorporate a steroid compound into the preparation, which has succeeded to some extent (Kligman, A. M. and Willis, I.: Arch. Dermatol., 111, 40–48, (1975)). However, such a preparation also produces undesirable side effects such as dermatrophy due to the steroid compound. Further, even if the steroid compound is incorporated into the preparation, the content of hydroquinone in the preparation is limited to at most about 5% because of its irritant action and hence, it is difficult to further increase the amount of hydroquinone in the preparation to enhance its favorable effect.

Additionally, hydroquinone is readily oxidized to cause browning of the preparation, which spoils commercial value of the preparation. Besides, the oxidation products of hydroquinone have severe irritant action to the skin and hence, they make the side effect of the preparation more severe. This also spoils the commercial value of the preparation. In order to prevent oxidation of hydroquinone, it has been also proposed to incorporate an antioxidant such as ascorbic acid into the preparation (Toshio Hamada: Hifu, 18 (3), 249–272, (1976)), but with less satisfactory results.

The present inventor has now surprisingly found that a fatty acid ester of hydroquinone is quite stable even without any specific stabilizer and hardly shows irritant action as demonstrated by Skin Irritation Test using guinea pig hereinafter and that the ester exhibits excellent depigmentation of the skin.

One object of the present invention is to provide a topical skin depigmenting composition having good stability. Another object of the present invention is to provide a topical skin depigmenting composition which does not irritate the skin. Still another object of the present invention is to provide a method of depigmentation of the skin using a fatty acid ester of hydroquinone.

These and other objects as well as advantages of the present invention will become apparent to those skilled in the art from the following description by reference to the accompanying drawing wherein:

FIG. 1 is a graph showing the variation of optical density of each sample solution at 420 nm with the elapse of time in Stability Test—1 hereinafter.

According to the present invention, there is provided a topical skin depigmenting composition which comprises as an active ingredient a fatty acid ester of hydroquinone of the formula:

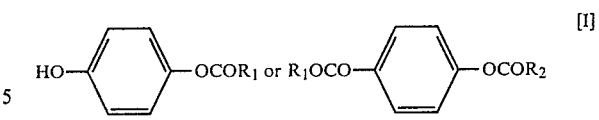

wherein $R_1$ and $R_2$ are the same or different, each being hydrogen or a straight or branched, saturated or unsaturated aliphatic hydrocarbon radical having 1 to 20 carbon atoms, provided that at least one of $R_1$ and $R_2$ is the hydrocarbon radical, and one or more conventional ingredients suitable for a topical preparation. The method of depigmentation of the present invention is effected by topically applying a composition containing as an active ingredient the fatty acid ester of hydroquinone of the formula [I] to the skin of a patient who needs depigmentation of the skin. Since the fatty acid ester of the hydroquinone of the formula [I] has no irritant action and high stability, the composition of the present invention needs no specific stabilizer and no steroid compound and can be used repeatedly for a long period of time without harmful side effects. Further, the amount of the active ingredient in the composition can be highly increased to exhibit its excellent depigmentation of the skin.

In order to demonstrate depigmentation activity, low irritant action and stability of the fatty acid ester of hydroquinone of the formula [I], the following tests were carried out.

(1) DEPIGMENTATION TEST

A pigment cell culture derived from B 16 mouse melanoma was cultivated in Petri dishes each containing Eagle's MEM liquid medium supplemented with 10% fetal bovine serum at 37° C. for 24 hours in a $CO_2$-incubator. Each fatty acid ester of hydroquinone of the formula [I] was then added to each Petri dish in such an amount that the concentration of the ester in the culture became 1 μg/ml and the dish was further incubated at 37° C. for 3 days. After incubation, the culture was fixed with 10% neutral formalin and subjected to dopa reaction. Melanin deposition was microscopically observed and graded as follows:

−: No melanin deposition was observed.
+: Melanin deposition was slightly observed.
++: Melanin deposition was remarkably observed.

The results are shown in Table 1. Besides, the same test was carried out by using hydroquinone or ascorbic acid instead of the fatty acid ester of hydroquinone as well as without addition of these compounds (control). The results thereof are also shown in Table 1.

TABLE 1

| Test compounds | Melanin deposition |
| --- | --- |
| Hydroquinone monocaprylate | − |
| Hydroquinone monolaurate | − |
| Hydroquinone monomyristate | − |
| Hydroquinone monopalmitate | − |
| Hydroquinone monostearate | − |
| Hydroquinone monooleate | − |
| Hydroquinone diacetate | − |
| Hydroquinone dipropionate | − |
| Hydroquinone dibutyrate | − |
| Hydroquinone divalerate | − |
| Hydroquinone | − |
| Ascorbic acid | ++ |
| Control | ++ |

As is seen from Table 1, the fatty acid ester of hydroquinone completely inhibits melanin production of the pigment cell culture in the same concentration as that of hydroquinone.

(2) SKIN IRRITATION TEST

Ointments containing various amounts of hydroquinone monopalmitate or hydroquinone dibutylate were applied to the shaved backs of guinea pigs once a day for 3 days. The irritation was visually observed and graded as follows:

—: No change was observed.
+: Erythema was observed.
++: Irritation was more severe than +.

The results are shown in Table 2. Besides, the same test was carried out by using ointments containing hydroquinone instead of the ester as well as ointments without these compounds (control). The results thereof are also shown in Table 2.

TABLE 2

| Test compounds | Concentration in ointment (%) | Irritation |
|---|---|---|
| Hydroquinone monopalmitate | 2 | — |
| " | 5 | — |
| " | 10 | — |
| " | 20 | ± |
| Hydroquinone dibutyrate | 2 | — |
| " | 5 | — |
| " | 10 | — |
| " | 20 | ± |
| Hydroquinone | 2 | + |
|  | 5 | ++ |
| Control |  | — |

As is seen from Table 2, the fatty acid ester of hydroquinone hardly irritates the skin.

(3) STABILITY TEST—1

Each fatty acid ester of hydroquinone was dissolved in 70% aqueous ethanol to obtain 1 mM solution of the ester. The solution was basified to pH 12 with 0.1N sodium hydroxide and maintained at 50° C. Optical density of the solution was measured at 420 nm with the elapse of time to observe coloration of the solution due to oxidation of the ester. The same test was carried out by using hydroquinone instead of the ester thereof. The results are shown in the accompanying FIG. 1. In FIG. 1, the ordinate axis indicates optical density at 420 nm and the transverse axis indicates time (min.). The curve 1 shows the results obtained by using the solution containing hydroquinone monopalmitate. Likewise, the curves 2, 3 and 5 show the results obtained by using the solutions containing hydroquinone monolaurate, hydroquinone diacetate and hydroquinone, respectively. The solutions containing hydroquinone dipropionate, hydroquinone dibutyrate and hydroquinone divalerate, respectively, gave the similar results as shown by the curve 4.

As is clear from FIG. 1, the solution containing hydroquinone is quickly colored by oxidation, while the solution containing the fatty acid ester thereof is quite stable in the water-ethanol system.

(4) STABILITY TEST—2

Absorption ointments prepared according to Japanese Pharmacopeia VIII, C-599 and containing hydroquinone monopalmitate or dibutyrate in various concentrations were allowed to stand at room temperature. Coloration of each ointment with the elapse of time was visually evaluated and graded as follows:

A: No coloration
B: Slightly colored
C: Remarkably colored

The same test was carried out by using the ointment containing hydroquinone or both hydroquinone and ascorbic acid instead of the fatty acid ester of hydroquinone.

The results are shown in Table 3.

TABLE 3

| Test compounds | Concentration (%) | Elapse of time | | | |
|---|---|---|---|---|---|
|  |  | 3 days | 1 week | 1 month | 3 months |
| Hydroquinone nomopalmitate | 5 | A | A | A | A |
|  | 10 | A | A | A | A |
|  | 20 | A | A | A | A |
| Hydroquinone dibutyrate | 5 | A | A | A | A |
|  | 10 | A | A | A | A |
|  | 20 | A | A | A | A |
| Hydroquinone | 5 | C | — | — | — |
| Hydroquinone + Ascorbic acid | 5 0.1 | B | C | — | — |

As is clear from Table 3, the fatty acid ester of hydroquinone is quite stable in the ointment.

The fatty acid ester of hydroquinone of the formula [I] used in the present invention can be prepared according to a standard esterification method, for example, by esterifying hydroquinone with a fatty acid chloride. Preferred examples of the ester of the formula [I] are hydroquinone monoacetate, hydroquinone monopropionate, hydroquinone monobutyrate, hydroquinone monovalerate, hydroquinone monocaprylate, hydroquinone monoundecanoate, hydroquinone monolaurate, hydroquinone monomyristate, hydroquinone monopalmitate, hydroquinone monostearate, hydroquinone monoisostearate, hydroquinone monooleate, hydroquinone diacetate, hydroquinone dipropionate, hydroquinone dibutyrate and hydroquinone divalerate. The fatty acid esters of hydroquinone of the formula [I] can be used alone or in the combination thereof. In view of the effect, it is preferable to use the fatty acid ester of hydroquinone in the amount of 0.01 to 50% by weight, more preferably, 0.5 to 20% by weight based on the total weight of the composition of the present invention.

The topical skin depigmenting composition of the present invention can be prepared in a conventional form known in the fields of drugs, quasi drugs and cosmetics such as an ointment, cream, lotion, pack, paste or the like according to a conventional technique. The other ingredient(s) of the composition are not specified and conventional ingredients such as solid or liquid carriers (e.g. waxes, starches, kaolin, cellulose, water, ethanol, etc.), thickeners, emulsifiers, perfumes, preservatives and the like can be used.

The composition of the present invention exhibits excellent depigmentation of the skin by topically applying it to the skin of a patient who needs depigmentation, for example, a patient who suffers from liver spots, freckles, post inflammatory pigmentation, Riehl's melanosis or pigmentation after sunburn.

The following Preparations, and Examples further illustrate the present invention in detail but are not to be construed to limit the scope thereof. In the Examples, all the "%'s" are by weight unless otherwise stated.

PREPARATION 1

Hydroquinone (440 g) was dissolved in a solution of sodium hydroxide (160 g) in water (1600 ml) and to the resulting solution was added dropwise a solution of acetyl chloride (346 g) in tetrahydrofuran (346 g), while maintaining the temperature at 0° C. with ice-cooling. After addition, the mixture was stirred at 0° C. for 1 hour and then at room temperature for 2 hours. The reaction mixture was extracted with ethyl acetate. The ethyl acetate extract was washed with a small amount of water. Ethyl acetate was removed and the residue was distilled under a reduced pressure to give hydroquinone monoacetate (188 g). b.p. 144°–147° C./4 mmHg.

TLC on a silica gel plate ($CHCl_3$/AcOEt (3:1), UV light) showed Rf 0.85.

PREPARATION 2

According to the same procedure as described in Preparation 1, hydroquinone and valeryl chloride were reacted and the reaction mixture was extracted with ethyl acetate. The ethyl acetate extract was washed with water and ethyl acetate was removed. The resulting residue was thoroughly washed with water to remove unreacted hydroquinone and distilled under a reduced pressure to give hydroquinone monovalerate. b.p. 163°–166° C./1 mmHg.

TLC on a silica gel plate ($CHCl_3$/AcOEt) (3:1), UV light) showed Rf 0.71.

PREPARATION 3

According to the same procedure as described in Preparation 1, hydroquinone and n-undecanoyl chloride (prepared by chlorination of n-undecanoic acid with thionyl chloride) were reacted and the reaction mixture was extracted with ethyl acetate. The ethyl acetate extract was concentrated and the residue was dissolved in n-hexane and crystallized with cooling to give crude hydroquinone monoundecanoate. The crude product was recrystallized from n-hexane. m.p. 72°–74° C.

TLC on a silica gel plate ($CHCl_3$/AcOEt (3:1), UV light) showed Rf 0.60.

PREPARATION 4

According to the same procedure as described in Preparation 1, hydroquinone and isostearoyl chloride (prepared by chlorination of isostearic acid with thionyl chloride) were reacted and the reaction mixture was extracted with ethyl acetate. The extract was washed with water and the solvent was removed. The resulting residue was thoroughly washed with water to remove unreacted hydroquinone and concentrated on a water bath at 70° C. under the reduced pressure of 1 mmHg to give hydroquinone monoisostearate.

TLC on a silica gel plate ($CHCl_3$/AcOEt (3:1), UV light) showed Rf 0.48.

PREPARATION 5

Hydroquinone (55 g) was dissolved in 10% sodium hydroxide solution (200 g) and to the resulting solution was added tetrahydrofuran (50 g). A solution of palmitoyl chloride (13.7 g) in tetrahydrofuran was added dropwise to the mixture over about 1 hour, while maintaining the temperature at 0° to 5° C. The reaction mixture was stirred at the same temperature for 1 hour and then at room temperature for 2 hours. The reaction mixture was poured into dil. sulfuric acid and extracted with ethyl acetate. The ethyl acetate extract was washed with water and concentrated under a reduced pressure. The concentrate was purified by silica gel column chromatography to give hydroquinone monopalmitate (10 g). m.p. 90.5°–91.5° C.

TLC on a silica gel plate ($CHCl_3$/acetone (2:1)) showed Rf 0.76.

PREPARATION 6

Hydroquinone (440 g) was dissolved in a solution of sodium hydroxide (80 g) in water (2000 ml). To the resulting solution was added dropwise a solution of n-capryloyl chloride (648 g) in tetrahydrofuran (600 ml) at up to 18° C. with vigorous stirring. After addition, stirring was continued for 1 hour and then the mixture was allowed to stand overnight at room temperature. The reaction mixture was filtered and the filtrate was extracted with ethyl acetate. The ethyl acetate extract was washed with water and the solvent was removed to give a crystalline product (165 g). The product was dissolved in ethyl acetate and the solution was washed with water to remove unreacted hydroquinone. The solvent was removed to give hydroquinone monocaprylate (36 g). m.p. 64°–65.5° C.

PREPARATION 7

According to the same procedure as described in Preparation 6, hydroquinone and propionyl chloride were reacted and the reaction mixture was extracted with ethyl acetate. The ethyl acetate extract was thoroughly washed with water and the solvent was removed. The residue was distilled under a reduced pressure to give hydroquinone monopropionate. b.p. 140°–142.5° C./3 mmHg, m.p. 68°–74° C.

PREPARATION 8

According to the same procedure as described in Preparation 6, hydroquinone and butyryl chloride were reacted and the reaction mixture was extracted with ethyl acetate. The ethyl acetate extract was thoroughly washed with water and the solvent was removed. The residue was distilled under a reduced pressure to give hydroquinone monobutyrate. b.p. 150°–153° C./3 mmHg.

PREPARATION 9

Hydroquinone (55 g) was dissolved in a solution of sodium hydroxide (20 g) in water (300 ml) and to the resulting solution was added dropwise a solution of tetradecanoyl chloride (123 g) in tetrahydrofuran (150 ml) with cooling. The precipitate formed was filtered off and the filtrate was extracted with ethyl acetate. The extract was thoroughly washed with water to remove unreacted hydroquinone and the solvent was removed. The residue was recrystallized from n-hexane to give hydroquinone monomyristate (20 g). m.p. 75°–78° C.

PREPARATION 10

Hydroquinone (110 g) was dissolved in a solution of sodium hydroxide (80 g) in water (400 ml) and to the resulting solution was added dropwise a solution of acetyl chloride (157 g) in tetrahydrofuran (157 g) with ice-cooling (0° C.). The reaction mixture was allowed to stand overnight at room temperature. The reaction mixture was poured into water (1 liter) and the crystals formed was filered and dissolved in chloroform. The solution was washed with dil. sodium hydroxide solution to remove unreacted hydroquinone. After removal of the solvent, the residue was recrystallized from water/ethanol to give hydroquinone diacetate (175 g). m.p. 121°–122.5° C.

PREPARATION 11

According to the same procedure as described in Preparation 10, hydroquinone (55 g), and propionyl chloride (92.52 g) were reacted to give hydroquinone dipropionate (105 g). m.p. 112°–114° C.

PREPARATION 12

Hydroquinone (55 g) was dissolved in a solution of sodium hydroxide (40 g) in water (300 ml) and to the resulting solution was added dropwise butyryl chloride (100 g), while maintaining the temperature at 3° to 6° C. The reaction was allowed to proceed at 10° to 13° C. for 4 hours. After reaction, the mixture was extracted with benzene and the benzene extract was washed with dil. sodium hydroxide solution. The solvent was removed from the extract and the residue was dissolved in ethanol (300 ml). Recrystallization was effected by addition of water (80 ml) to the solution to give hydroquinone dibutyrate (108 g). m.p. 42°–43° C.

PREPARATION 13

Hydroquinone (45.6 g) was dissolved in a solution of sodium hydroxide (33.2 g) in water (332 ml) and to the resulting solution was added dropwise valeryl chloride (100 g), while maintaining the temperature at 3° to 6° C. The reaction was allowed to proceed at 15° C. for 1 hour. After reaction, the mixture was extracted with benzene and the benzene extract was washed with dil. sodium hydroxide solution to remove unreacted hydroquinone. The solvent was removed from the extract and the residue was distilled under a reduced pressure to give crude crystals (40 g) which were recrystallized from ethanol to give hydroquinone divalerate (36 g). b.p. 155°–157° C./1 mmHg.

EXAMPLE 1

According to the following formulation, the topical skin depigmenting composition of the present invention in the form of a cream was prepared by a conventional technique.

| Ingredients | % |
| --- | --- |
| Liquid paraffin | 41.00 |
| Vaseline | 15.00 |
| Beeswax | 10.00 |
| Solid wax | 6.00 |
| Glycerol monostearate | 2.00 |
| Polyoxyethylene sorbitan monooleate | 2.00 |
| Stearic acid | 0.10 |
| Borax | 0.20 |
| Hydroquinone monostearate | 5.00 |
| Perfume | q.l. |
| Preservative | q.l. |
| Water | 18.70 |

Likewise, when the same amount of hydroquinone monoacetate, hydroquinone monoundeacanoate or hydroquinone divalerate was used instead of hydroquinone monostearate in the above formulation, the topical composition of the present invention in the form of a cream was obtained.

EXAMPLE 2

According to the following formulation, the topical skin depigmenting composition of the present invention in the form of a lotion was prepared by a conventional technique.

| Ingredients | % |
| --- | --- |
| Ethanol | 10.00 |
| Polyvinyl pyrrolidone | 0.05 |
| Oleyl alcohol | 0.10 |
| Polyoxyethylene sorbitane monolaurate | 1.20 |
| Propylene glycol | 5.00 |
| Hydroquinone monopalmitate | 0.10 |
| Perfume | q.l. |
| Preservative | q.l. |
| Water | 83.55 |

Likewise, when the same amount of hydroquinone monopropionate, hydroquinone monomyristate or hydroquinone dibutyrate was used instead of hydroquinone monopalmitate in the above formulation, the topical skin depigmenting composition of the present invention in the form of a lotion was obtained.

EXAMPLE 3

According to the following formulation, the topical skin depigmenting composition of the present invention in the form of a pack was prepared by a conventional technique.

| Ingredients | % |
| --- | --- |
| Kaolin | 65.00 |
| Starch | 19.00 |
| Propylene glycol | 5.00 |
| Calcium acetate | 0.01 |
| Uric acid | 0.50 |
| Hydroquinone monopalmitate | 10.00 |
| Perfume | 0.49 |

Likewise, when the same amount of hydroquinone monobutyrate, hydroquinone monomyristate or hydroquinone dipropionate was used instead of hydroquinone monopalmitate in the above formulation, the topical skin depigmenting composition of the present invention in the form of a pack was obtained.

EXAMPLE 4

According to the following formulation, the topical skin depigmenting composition of the present invention in the form of a milky lotion by a conventional technique.

| Ingredients | % |
| --- | --- |
| Stearic acid | 1.70 |
| Cetanol | 0.50 |
| Lanolin | 2.00 |
| Oleyl oleate | 2.00 |
| Squalane | 3.00 |
| Liquid paraffin | 8.00 |
| Hydroquinone monostearate | 0.50 |
| Emulsifier | 2.60 |
| Triethanolamine | 1.00 |
| Propylene glycol | 4.00 |
| Perfume | q.l. |
| Preservative | q.l. |
| Water | 74.90 |

Likewise, when the same amount of hydroquinone monovalerate, hydroquinone monoisostearate or hydroquinone divalerate was used instead of hydroquinone monostearate in the above formulation, the topical composition of the present invention in the form of a milky lotion was obtained.

EXAMPLE 5

According to the following formulation, the topical skin depigmenting composition of the present invention in the form of a paste was prepared by a conventional technique.

| Ingredients | % |
| --- | --- |
| Polyoxyethylene sorbitan distearate | 15.00 |
| Polyoxyethylene sorbitan monooleate | 2.00 |
| Microcrystalline cellulose | 1.00 |
| Glycerin | 10.00 |
| Hydroxyethyl cellulose | 4.00 |
| Hydroquinone monolaurate | 20.00 |
| Preservative | q.l. |
| Water | 48.00 |

Likewise, when the same amount of hydroquinone monocaprylate, hydroquinone monooleate or hydroquinone diacetate was used instead of hydroquinone monolaurate in the above formulation, the topical composition of the present invention in the form of a paste was obtained.

What is claimed is:

1. A method for depigmentation of skin which comprises topically applying to the skin of a patient requiring depigmentation a cosmetic carrier selected from the group consisting of ointments, creams, lotions, packs and pastes, containing an amount of fatty acid ester of hydroquinone of the formula:

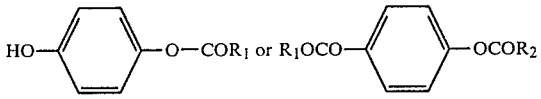

wherein $R_1$ and $R_2$ are the same or different, each being a straight or branched, saturated or unsaturated aliphatic hydrocarbon radical having 1 to 20 carbon atoms, effective to depigment the skin.

* * * * *